(12) United States Patent
Muya et al.

(10) Patent No.: US 9,591,850 B2
(45) Date of Patent: Mar. 14, 2017

(54) COMPOSITIONS AND METHODS FOR DISINFECTING AND CLEANING CONTACT LENSES

(71) Applicant: Novartis AG, Basel (CH)

(72) Inventors: Leroy Wainaina Muya, Duluth, GA (US); Howard Allen Ketelson, Dallas, TX (US)

(73) Assignee: NOVARTIS AG (CH)

( * ) Notice: Subject to any disclaimer, the term of this patent is extended or adjusted under 35 U.S.C. 154(b) by 56 days.

(21) Appl. No.: 14/496,044

(22) Filed: Sep. 25, 2014

(65) Prior Publication Data

US 2015/0093452 A1 Apr. 2, 2015

Related U.S. Application Data

(60) Provisional application No. 61/883,365, filed on Sep. 27, 2013.

(51) Int. Cl.
*A01N 25/30* (2006.01)
*A01N 59/00* (2006.01)
*A61L 12/12* (2006.01)

(52) U.S. Cl.
CPC ............. *A01N 25/30* (2013.01); *A01N 59/00* (2013.01); *A61L 12/128* (2013.01)

(58) Field of Classification Search
None
See application file for complete search history.

(56) References Cited

U.S. PATENT DOCUMENTS

| | | | |
|---|---|---|---|
| 2,174,761 A | 10/1939 | Schuette | |
| 2,828,345 A | 3/1958 | Spriggs | |
| 4,812,173 A | 3/1989 | Tsao | |
| 4,889,689 A | 12/1989 | Tsao | |
| 5,523,012 A | 6/1996 | Winterton | |
| 5,746,972 A | 5/1998 | Park | |
| 7,022,654 B2 | 4/2006 | Tsao | |
| 8,318,144 B2 | 11/2012 | Ketelson | |
| 2008/0138310 A1 | 6/2008 | Ketelson | |
| 2011/0008276 A1 | 1/2011 | Davis | |
| 2011/0059039 A1 | 3/2011 | Ketelson | |
| 2011/0151017 A1 | 6/2011 | Ketelson | |
| 2011/0300019 A1 | 12/2011 | Davis | |

FOREIGN PATENT DOCUMENTS

WO 2008073909 A2 6/2008

OTHER PUBLICATIONS

Ward, Soft Contact Lens Care Products, Contact Lens Spectrum (2003), pp. 1-6.*
PCT International Search Report dated Mar. 24, 2015, International Application No. PCT/US2014/057354, International Filing Date Sep. 25, 2014.
PCT Written Opinion of the International Searching Authority dated Mar. 24, 2015, International Application No. PCT/US2014/057354, International Filing Date Sep. 25, 2014.
Authors: Alison D. Bedells, Rana M. Arafeh, Zhuo Yang, David Attwood, Frank Heatley, John C. Padget, Colin Price and Colin Booth Title: Micellisation of Diblock Copoly(oxyethylene/oxybutylene) in Aqueous Solution Published: J. Chem. Soc. Faraday Trans. 1993, vol. 89(8), pp. 1235-1242.
Authors: Chiraphon Chaibundit, Shao-Min Mai, Frank Heatley, and Colin Booth Title: Association Properties of Triblock Copolymers in Aqueous Solution: Copolymers of Ethylene Oxide and 1,2-Butylene Oxide with Long E-blocks Published: Langmuir 2000, vol. 16, pp. 9645-9652.
Authors: Antonis Kelarakis, Vasiliki Havredaki, Ga-Er Yu, Leo Derici and Colin Booth Title: Temperature Dependences of the Critical Micelle Concentrations of Diblock Oxyethylene/Oxybutylene Copolymers, A Case of Athermal Micellization Published: Macromolecules 1998, vol. 31, pp. 944-946.
Authors: Howard A. Ketelson, David L. Meadows, Ralph P. Stone Title: Dynamic wettability properties of a soft contact lens hydrogel Published: Colloids and Surfaces B: Biointerfaces, vol. 40 (2005) pp. 1-9.
Authors: V.M.Nace Title: Contrasts in the Surface Activity of Polyoxypropylene and Polyoxybutylene-Based Block Copolymer Surfactants Published: JAOCS (1996) vol. 73. No. 1, pp. 1-8.
Authors: Ga-Er Yu, Yung-Wei Yang, Zhuo Yang, David Attwood, Colin Booth, and V. Mark Nace Title: Association of Diblock and Triblock Copolymers of Ethylene Oxide and Butylene Oxide in Aqueous Solution Published: Langmuir 1996, vol. 12, pp. 3404-3412.
Authors: Yung-Wei Yang, Nan-Jie Deng, Ga-Er Yu, Zu-Kang Zhou, David Attwood and Colin Booth Title: Micellization of Diblock and Triblock Copolymers in Aqueous Solution. New Results for Oxyethylene/Oxybutylene Copolymers E38B12 and E21B11E21. Comparison of Oxyethylene/Oxybutylene, Oxyethylne/Oxypropylene, and Oxyethylene/Alkyl Systems Published: Langmuir 1995, vol. 11, pp. 4703-4711.
Authors: Zhuo Yang, Simon Pickard, Nan-Jie Deng, Raymond J. Barlow, David Attwood and Colin Booth Title: Effect of Block Structure on the Micellization and Gelation of Aqueous Solutions of Copolymers of Ethylene Oxide and Butylene Oxide Published: Macromolecules 1994, vol. 27, pp. 2371-2379.
Authors: Joseph Z. Krezanoski, Ph.D., R. Dennis Houlsby, M.A. Title: A comparison of new hydrogen peroxide disinfection systems Published: Journal of the American Optometric Association, vol. 59, No. 3, 3/88, pp. 193-197.

* cited by examiner

*Primary Examiner* — Abigail Fisher
*Assistant Examiner* — Frank Choi
(74) *Attorney, Agent, or Firm* — Sheng-Hsin Hu

(57) ABSTRACT

This invention relates generally to disinfection and cleaning systems for medical devices. In a preferred embodiment, the invention relates to compositions, methods and articles for simultaneously cleaning and disinfecting contact lenses. The present invention is directed to ophthalmic compositions containing one or more block copolymers referred to as (polyoxyethylene)-(poly-oxybutylene) block copolymers ("PEO-PBO"). The invention is particularly directed to the use of PEO-PBO di-block copolymers as non-foaming wetting agents in peroxide-based compositions for disinfecting contact lenses.

11 Claims, No Drawings

COMPOSITIONS AND METHODS FOR DISINFECTING AND CLEANING CONTACT LENSES

This application claims the benefit under 35 USC §119 (e) of U.S. provisional application No. 61/883,365 filed 27 Sep. 2013, incorporated by reference in its entirety.

FIELD OF THE INVENTION

This invention relates generally to disinfection and cleaning systems for medical devices. In a preferred embodiment, the invention relates to compositions, methods and articles for simultaneously cleaning and disinfecting contact lenses. The present invention is directed to ophthalmic compositions containing one or more block copolymers referred to as (polyoxyethylene)-(poly-oxybutylene) di-block copolymers ("PEO-PBO"). The invention is particularly directed to the use of PEO-PBO di-block copolymers as non-foaming wetting agents in peroxide-based compositions for disinfecting contact lenses.

BACKGROUND OF THE INVENTION

Disinfecting solutions for use with contact lenses are well known in the art and the use of such lenses involves a daily disinfecting treatment regimen. The two most common methods of contact lens disinfection, cleaning and storage are multi-purpose disinfecting solutions and hydrogen peroxide-based solutions. The multi-purpose disinfecting solutions contain preservatives but hydrogen peroxide-based systems contain no preservative after hydrogen peroxide is neutralized and converted to Oxygen and water. Hydrogen peroxide is an effective microbial disinfectant, destroying pathogens by oxidation. Hydrogen peroxide systems, particularly 3% hydrogen peroxide solutions, have increasingly become popular as the disinfectant of choice for all types of daily and extended wear hydrogel lenses. The primary reason for their popularity is the rapid kill of microbial contaminants and low-residual hydrogen peroxide following the cleaning and disinfection regimen time. During hydrogen peroxide disinfection of lenses the natural and innocuous by products, O2 and water, are generated. See Krezanoski et al., "Journal of the American Optometric Association", Vol. 59, Number 3, pages 193 197 (1988). In general, the hydrogen peroxide systems involve a hydrogen peroxide-containing disinfecting solution into which the contact lenses to be disinfected are placed and allowed to remain for a required period of time. The hydrogen peroxide may (1) oxidize chloride in the bacteria to hypochlorite or (2) decompose into nascent oxygen and hydroxyl radicals, thus providing a germicidal effect. Following the requisite time period a purposeful inactivation of the hydrogen peroxide is conducted, for example, with a platinum catalyst. Following inactivation, the contact lens may be safely re-inserted into the eye.

Contact lenses may be broadly divided into two categories: rigid gas permeable lenses, and soft, hydrogel lenses, although hybrids and other types of lenses exist. Soft or hydrogel lenses have become popular partly because they are comfortable to wear and require a shorter period of adaptation. Hydrogels are water swollen three-dimensional polymeric networks that are used in a variety of biomedical applications including drug delivery agents, prosthetic devices and contact lenses. The surface characteristics of hydrogels are partly determined by the orientation of hydrophobic and hydrophilic moieties of the macromolecules. See, e.g., Ketelson et al., Colloids and Surfaces B: Biointerfaces. Vol. 40. pages 1-9 (2005).

Because contact lenses are in intimate contact with the corneal surface and the human tear film, which is composed mainly of proteins, lipids, ions and mucins, the biocompatibility characteristics of the lenses are directly affected by the surface wettability properties of the hydrogel materials. In particular, evaluating the surface wettability properties of a lens material is important because such properties may affect the lens insertion and daily comfort. To maintain a stable tear film, a contact lens material must have hydrophilic surface properties. If the contact lens material exhibits mostly hydrophobic properties on the lens surface, the tear film may be disrupted. To determine the wettability of a surface via an aqueous solution, such as human lacrimal fluid, i.e., tears, the contact angle is measured. The spread of an aqueous fluid on a surface indicates that the surface exhibits a degree of hydrophilicity, thereby resulting in a low contact angle. The surface is hydrophobic if a drop of aqueous fluid does not spread, thereby resulting in a high contact angle. A new family of contact lens materials, silicone hydrogels, is replacing traditional hydrogels as the material of choice for extended wear soft contact lenses. Silicone hydrogel materials have significantly higher oxygen permeability than traditional soft lens hydrogels due to the presence of silicone functional groups. Additionally, the presence of silicone groups in silicone hydrogel materials results in a lens surface having hydrophobic properties.

Various techniques, for example, plasma surface treatments and incorporation of wetting agents within the lens material, have been utilized in order to provide a biocompatible, hydrophilic and wettable lens surface. An example of a silicone hydrogel lens with surface treatment is the AIR OPTIX™ contact lenses marketed by Alcon. These lenses are plasma coated. Although modifying the surface can improve biocompatibility, it has also been reported that some silicone hydrogel materials accumulate lipids over time, and that this build-up may result in a decrease in the wettability of the silicone hydrogel lens material and surface.

The wettability characteristics of the surfaces of contact lenses may also be modified by reducing the amount of hydrophobization on the surfaces. Surfactants have been utilized in prior compositions for treating contact lenses, for example, poloxamers and poloxamines, such as the Pluronic® and Tetronic® brands of surfactants, which are poly(oxyethylene)-poly(oxypropylene) ("PEO-PPO") block copolymers, have been used extensively in prior products utilized to treat contact lenses. However, U.S. Patent application Publication No. 2011/0300019 (Ketelson et al.) discloses that such surfactants do not wet silicone hydrogel lenses efficiently.

U.S. Pat. No. 5,523,012 to Winterton, et al. teaches that the addition of a surface-active agent to a peroxide disinfection solution will enhance the disinfecting properties of the solution. However, the surfactants disclosed are all present in amounts above 0.1% and, because of excessive foaming, are incompatible with the platinum catalyst disc typically used to deactivate hydrogen peroxide in the lens disinfection systems.

U.S. Pat. No. 5,423,012 to Winterton discloses buffered peroxide formulations with poloxamine or poloxamer surface active agents.

U.S. Pat. No. 5,746,972 to Park, et al. teaches compositions and methods for disinfecting and cleaning contact lenses include a liquid medium containing hydrogen peroxide and a solid ethylene oxide/propylene oxide block copolymer surfactant having at least 70% by weight polyethylene oxide. The hydrogen peroxide is degraded by a catalase released into the solution and causes "a reduced amount of foam." However, such compositions cause excessive foaming when a platinum catalyst is used to decompose the hydrogen peroxide.

A new class of surface-active agents has been found to efficiently wet silicone hydrogel lenses, namely, EO-BO copolymers. However, it has been found that EO-BO copolymers may cause excessive foaming when used in peroxide-based disinfecting solutions during neutralization, for example, with platinum catalyst discs.

U.S. Patent Application Publication No. 2008/0138310 (Ketelson et al.) is discloses the use of poly(oxyethylene)-poly(oxybutylene) block copolymers in pharmaceutical compositions.

In view of the foregoing, there is a need for new methods and compositions for improving the wettability of silicone hydrogel contact lenses as well as older lens types while minimizing foaming of peroxide-based contact lens disinfection formulations.

SUMMARY OF THE INVENTION

The present invention, in one aspect, provides a composition for disinfecting a contact lens, comprising about 0.5 w/v % to about 6 w/v % by weight hydrogen peroxide and at least one poly(oxyethylene)-poly(oxybutylene) di-block copolymer, wherein the poly(oxyethylene)-poly(oxybutylene) di-block copolymer is of the formula $(EO)_m(BO)_n$, wherein EO is oxyethylene and BO is oxybutylene, and wherein m is an integer having an average value of 5 to 15 and n is an integer having an average value of 2 to 10, wherein the composition is incapable of foaming at any time within a disinfection cycle carried out in a disinfection cup having a platinum-coated plastic disk that catalytically decomposes hydrogen peroxide generating oxygen gas bubbles excessively to cause overflow of the composition from the disinfection cup.

The present invention, in another, provides a method of disinfecting a contact lens comprising the steps of: (a) contacting a contact lens with an aqueous solution of about 0.5 w/v % to about 6 w/v % by weight hydrogen peroxide and at least one poly(oxyethylene)-poly(oxybutylene) di-block copolymer, wherein the poly(oxyethylene)-poly(oxybutylene) di-block copolymer is of the formula $(EO)_m(BO)_n$, wherein EO is oxyethylene and BO is oxybutylene, and wherein m is an integer having an average value of 5 to 15 and n is an integer having an average value of 2 to 10, wherein the composition is incapable of foaming at any time within a disinfection cycle carried out in a disinfection cup having a platinum-coated plastic disk that catalytically decomposes hydrogen peroxide generating oxygen gas bubbles excessively to cause overflow of the composition from the disinfection cup, and (b) neutralizing said hydrogen peroxide by catalytic decomposition.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

The abbreviation "PEO-PPO" means poly(oxyethylene)-poly(oxypropylene).

The abbreviation "PEO-PBO" means poly(oxyethylene)-poly(oxybutylene).

The abbreviation "PEO-PBO-PEO" means poly(oxyethylene)-poly(oxybutylene)-poly(oxyethylene).

The abbreviation "PEG" means polyethylene glycol. The abbreviation "b.d.l." means below detection limit.

The abbreviation "PHMB" means polyhexamethylene biguanide.

The abbreviation "mOsm/kg" means milliosmoles/kilogram of water.

The abbreviation "HLB" means hydrophilic-lipophilic balance.

The abbreviation "EO" means oxyethylene.

The abbreviation "BO" means oxybutylene.

The term "contact angle" is a quantitative measure of the wetting of a solid by a liquid and defined geometrically as the angle formed by a liquid where liquid, gas and solid phases intersect. Alternative, related terms that may be used herein include "wetting angle" or "advancing contact angle."

The term "hydrophilic" means having a strong affinity for water. Alternative, related terms that may be used herein include "hydrophilicity".

The term "hydrophobic" means to have little or no affinity for water. Alternative, related terms that may be used herein include, "hydrophobicity".

The term "surfactant" means a substance capable of reducing the surface tension of a liquid, e.g., water or an aqueous solution, in which the substance is dissolved.

The term "wetting" means converting a hydrophobic surface whereon a liquid (e.g., water) does not spread because the liquid has an increased surface tension to a surface that is hydrophilic whereon the liquid spreads readily because its surface tension is reduced, as determined by a contact angle experiment. Alternative, related terms that may be used herein include "wettability".

The term "uptake" refers to the amount of surfactant that is absorbed and/or adsorbed by a contact lens or other medical device. Alternative terms that may be used herein include, "uptake concentration", "surfactant uptake", "uptake results", "uptake data" and "uptake concentration of surfactants".

The term "oxyethylene" means a two carbon alkenyl group bonded to an oxygen atom, for example —$CH_2$—$CH_2O$.

The term "oxybutylene" means a four carbon alkenyl group bonded to an oxygen atom, for example, —[OCH2C (CH2CH3)H]—.

The term "block copolymer" is a polymer that has at least one homopolymeric chain of one monomer and at least one additional homopolymeric chain of a second monomer. Exemplary configurations of such block copolymers include branched, star, di-block, tri-block and cyclic.

The term "homopolymer" means a polymer formed from a single monomer; for example, polyethylene formed by polymerization of ethylene.

The term "an amount effective to preserve" means an amount of an antimicrobial agent effective in producing the desired effect of preserving the solutions described herein from microbial contamination, preferably an amount which, either singly or in combination with one or more additional antimicrobial agents, is sufficient to satisfy the preservative efficacy requirements of the United States Pharmacopoeia ("USP").

The term "an amount effective to disinfect" means an amount of antimicrobial agent effective in producing the desired effect of disinfecting contact lenses by substantially reducing the number of viable microorganisms present on the lenses, preferably an amount which, either singly or in combination with one or more additional antimicrobial agents, is sufficient.

The term "an amount effective to clean" means an amount of a cleaning agent that facilitates removing, and is preferably effective to remove debris or deposit material from a contact lens contacted with the cleaning agent containing composition.

The term "ophthalmically acceptable vehicle" means a pharmaceutical composition having physical properties (e.g., pH and/or osmolality) that are physiologically compatible with ophthalmic tissues.

The present invention is partly based on the discovery that EO-BO di-block copolymers can be used in peroxide-based disinfecting solutions if EO-BO di-block copolymers have a narrow range of molecular weight from about 400 to about 1400. Relatively low molecular weight EO-BO di-block copolymers used in peroxide-based disinfecting solutions not only can effectively wet silicone hydrogel lenses but also do so without causing excessive foaming when used in peroxide-based disinfecting solutions during neutralization, for example, with platinum catalyst discs. It is an unexpected result since US2011/0300019 specifically pointed out that a new class of surface-active agents has been found to efficiently wet silicone hydrogel lenses, namely, BO-EO-BO copolymers. However, it has been found that BO-EO-BO copolymers may cause excessive foaming when used in peroxide-based disinfecting solutions during neutralization, for example, with platinum catalyst discs.

The present invention is directed to the use of block copolymers referred to as (polyoxyethylene)-(polyoxybutylene) di-block copolymers ("PEO-PBO") to modify the surface properties of ophthalmic medical devices, so as to enhance the wettability of the devices, and facilitate cleaning of the devices. The PEO-PBO di-block copolymers described herein may be contained in various types of compositions for treating medical devices, such as wetting solutions, soaking solutions, cleaning and comfort solutions, and disinfection solutions. The primary function of the PEO-PBO di-block copolymers in the compositions of the present invention is to treat the surface of a medical device, particularly an ophthalmic device, such as a contact lens or an intraocular lens. Such treatment facilitates the wettability of the device and/or the cleaning of the device. This surface treatment has been found to be particularly effective relative to enhancing the wettability of silicone hydrogel contact lenses. The present invention is partly based on a finding that certain PEO-PBO di-block copolymers can be used with peroxide-based contact lens formulations to effectively modify contact lens surface properties at low concentrations, for example, improving the wetting properties of silicone hydrogel contact lenses, without causing excessive foaming during platinum-induced neutralization.

Wettability may be determined by measuring the contact angle from the Young-Dupre equation as follows:

$$\gamma_{LV} \cos \theta = \gamma_{SV} - \gamma_{SL}$$

where γ is the interfacial tension between two phases indicated by the subscripts (S: solid, L: liquid, and V: vapor). Increasing $\gamma_{SL}$ and/or $\gamma_{Lv}$ increases the contact angle θ. For example, a water droplet beads up on a hydrophobic surface, displaying high contact angle at the water-solid interface (e.g. a contact lens surface soaked in saline). Water spreads out over a hydrophilic surface displaying low contact angles (e.g. a contact lens soaked in a surfactant solution).

The solution of the invention contains hydrogen peroxide in a concentration that is suitable for disinfecting purposes, preferably about 0.5% to about 6%, more preferably about 2% to about 6% by weight, most preferably between 3% and 4%, or about 3% by weight.

When a surfactant is present in a peroxide solution, foaming may occur due to the release of oxygen from the neutralization effect of the peroxide with the catalyst. The volume of foam can be substantial and when the amount of foaming is excessive the foaming may interfere with the procedures necessary to effectively disinfect a contact lens, for example, when the volume of foam exceeds the dimensions of the container used.

The block copolymers utilized in the present invention comprise compounds that contain hydrophilic and hydrophobic segments that can be altered to control the HLB (hydrophilic-lipophilic balance), molecular weight and other properties of the block copolymers using well known anionic polymerization techniques. More particularly, the di-block copolymers of the present invention are those that include a poly(oxyethylene) block as the hydrophilic component and a poly(oxybutylene) block as the hydrophobic component. These copolymers may also be described in terms of the approximate or average value assigned to the respective repeating group. For example, $(EO)_{10} (BO)_5$, where the average value of the oxyethylene group is 10, and the average value of the oxybutylene group is 5.

Preferred polymers of the present invention are di-block copolymers of the following general formula:

$$(EO)_m(BO)_n \quad \text{(I)}$$

wherein m is an integer having an average value of 5 to 15 and n is an integer having an average value of 2 to 10.

PEO-PBO di-block copolymers of the following general formula are particularly preferred:

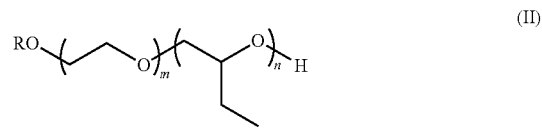

(II)

wherein R is selected from the group consisting of hydrogen, methyl, ethyl, propyl and butyl; m is an integer having an average value of 5 to 15; and n is an integer having an average value of 2 to 10.

Most preferred is a copolymer of formula (II) wherein R is methyl; m has an average value of 10; and n has an average value of 5.

The PEO-PBO di-block copolymers utilized in the present invention have a molecular weight in the range of 400 to about 1400 Daltons; and more preferably in the range of 700 to about 900 Daltons. Maintaining a proper hydrophilic-lipophilic balance (HLB) imparts certain properties to the PEO-PBO co-polymer compositions of the present invention. For example, the HLB of the di-block co-polymers utilized in the compositions of the present invention is directly related to the solubility, surface wettability, and interfacial surface activity properties of the compositions of the present invention.

The BO portion of the block copolymer of formula (I) is hydrophobic and is primarily responsible for the hydrophobic interactions of the compositions described herein. The EO portion of the copolymer provides the compositions with hydrophilic properties. More importantly, it is this portion of the co-polymer, in combination with the ratio of the BO portion significantly impacts the aqueous solubility of the copolymers. Although it is possible to utilize solubilizing agents in the compositions of the present invention, in which case the ratio of the EO to BO segments is somewhat less critical, it is preferred to utilize copolymers that do not require solubilizing agents, as such compounds may modify the HLB, which in turn may adversely affect the wettability properties of the compositions, cause ocular irritation, or create other concerns. Therefore, the preferred copolymers of formula (I) are those wherein there is a predominance of EO to BO segments. That is, the variable "m" in formula (I) and formula (II) above is preferably greater than the variable "n". The PEO-PBO block co-polymers will preferably have a ratio of EO to BO segments of from about 1:1 to about 3:1, with a ratio of about 1.5:1 to about 2:1 being most preferred.

The foregoing PEO-PBO block copolymers may be prepared by the application or adaptation of known methods described in the literature, for example, as described in Nace, V. M. *J. Am. Oil Chem. Soc.* 1996, 73, !; Yang, Z.; Pickard, S.; Deng, N.-J.; Barlow, R. J.; Attwood, D.; Booth, C. *Macro-molecules* 1994, 27, 2371; Yang, Y.-W.; Deng, N.-J.; Yu, G.-E.; Zhou, Z.-K.; Attwood, D.; Booth, C. *Langmuir* 1995, 11, 4703; Yu, G.-E.; Yang, Y.-W.; Yang, Z.; Attwood, D.; Booth, C.; Nace, V. M. *Langmuir* 1996, 12, 3404; Chaibundit, C.; Mai, S.-M.; Heatley, F.; Booth, C. *Langmuir* 2000, 16, 9645; Bedells, A. D.; Arafeh, R. M.; Yang, Z.; Attwood, D.; Heatley, F.; Pedget, J. C.; Price, C.; Booth, C. *J. Chem. Soc. Faraday Trans.* 1993, 89, 1235; and Kelarakis, A.; Havredaki, V.; Yu, G.-E.; Derici, L.; Booth, C. *Macromolecules* 1998, 31, 944, the entire contents of each of which are hereby incorporated in the present specification by reference. The foregoing PEO-PBO block copolymers may also be prepared by the application or adaptation of known methods described in U.S. Pat. No. 2,828,345 (Spriggs), and U.S. Pat. No. 2,174,761 (Schuette et al.), the entire contents of each of which are hereby incorporated into the present specification by reference.

The PEO-PBO block copolymers described above may be synthesized using a well-defined polyethylene glycol (PEG) polymer by controlled addition of oxybutylene to the primary hydroxyl group of the PEG polymer. For example, the PEO-PBO di-block copolymer $(EO)_{45} (BO)_{10}$ may be prepared according to the following general reaction scheme

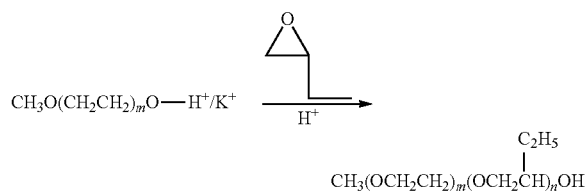

The above-described block copolymers and variations thereof may be used in combination, either with each other, or with other types of polymers. For example, PEO-PBO block copolymers or variations thereof may be used in combination with nonionic surfactants (e.g., poloxamer and poloxamine block copolymers, such as the Tetronic® brand of surfactants available from BASF) to provide additive or synergistic effects where appropriate. In a preferred embodiment, the PEO-PBO block polymers of the present invention are used in combination with poloxamine block copolymers. The PEO-PBO block copolymers may also be functionalized with specific end groups for specific surface reactions to covalently bind the polymer to a surface or prepare a new polymer material. The PEO-PBO block copolymers that may be utilized in the present invention are not limited relative to structure or molecular weight, so long as the block copolymers are soluble in aqueous solutions and are non-toxic to ophthalmic tissue at concentrations on the order of those described herein.

The amount of PEO-PBO di-block copolymer required in the compositions of the present invention will vary depending on the particular block copolymer selected and the purpose or function for which the block copolymer is being utilized (e.g., contact lens cleaning, contact lens wetting and/or inhibition of uptake of lipids or other biomolecules), as well as on other variables, such as the identity and physical properties of other components in the compositions. The determination of the ideal concentration of a particular copolymer in a given composition can be determined through routine testing. Such concentrations are referred to herein by means of the function to be performed by the PEO-PBO di-block copolymers, such as, "an amount effective to clean", "an amount effective to enhance wettability", "an amount effective to inhibit the uptake of biomolecules", and so on.

The total amount of PEO-PBO di-block copolymers contained in the compositions of the present invention will typically be in the range of 0.001 to about 0.5 weight/volume percent ("w/v %"), preferably about 0.01 to 0.3 w/v %, and more preferably between 0.04 to 0.1 w/v %.

It is to be noted that the surfactant of the hydrogen peroxide solution may be only one surfactant of the PEO-PBO di-block copolymers described above or a mixture of two or more surfactants, with the provision that no mixture of surfactants is capable of foaming at any time within a disinfection cycle carried out in a disinfection cup having a platinum-coated plastic disk that catalytically decomposes hydrogen peroxide generating oxygen gas bubbles excessively to cause overflow of the composition from the disinfection cup.

Many suitable surfactants can be used to form a mixture of surfactants with PEO-PBO di-block copolymers surfactant. For example the composition may also contain one or more poly(oxyethylene)-poly(oxypropylene) block copolymers such as poloxamer or poloxamine copolymers (e.g., poloxamine 1304, which is commercially available as "Tetronic® 1304"). Poloxamers, also known by the trade name Pluronic™, are nonionic block copolymers composed of a central hydrophobic chain of poly(oxypropylene) flanked by two hydrophilic chains of poly(oxyethylene). In the case of reverse Pluronics™, these are composed of a central hydrophilic chain of poly(oxyethylene) chain, flanked by two hydrophobic chains of poly(oxypropylene). Poloxamines, also known by the trade name Tetronic™, are tetra functional block copolymers which contain four polyethylene oxides (PEO)-polypropylene oxide (PPO) chains joined to the nitrogen atoms of a central ethylene diamine moiety.

The preferred surfactant used to form a mixture of surfactants with PEO-PBO block copolymers surfactant is a block copolymer of ethylene oxide and propylene oxide having the formula:

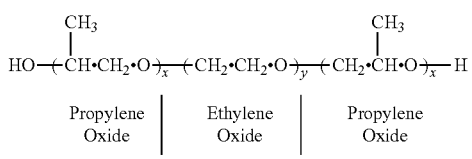

wherein x and y are integers from 1 to 350 reflecting the respective polyethylene oxide and polypropylene oxide blocks of said copolymer. The polyoxyethylene component of the block copolymer constitutes from 10 to 90 weight percent of the block copolymer. Preferably, the polyoxyethylene component of the block copolymer constitutes from 10 to 50 weight percent of the block copolymer. In another preferred embodiment of the present invention, the polyoxyethylene component of the block copolymer constitutes less than 50 weight percent of the block copolymer. Most preferably, the polyoxyethylene component of the block copolymer constitutes about 40 weight percent of the block copolymer. A particularly preferred embodiment of the present invention is a composition comprising Pluronic® 17R4 (available from BASF Corporation). Surfactants of poly(oxyethylene)-poly(oxypropylene) block copolymers having a total molecular weight of 1000 to about 20000 are preferred. More preferred are those surfactants having a molecular weight of 1200 to 3100. Most preferred are those surfactants having a molecular weight of about 2650.

The total amount of surfactant components including in the composition varies over a wide range depending on a number of factors, for example, the specific surfactant or surfactants being used, the other components in the composition and the like. Often the total amount of surfactant is in the range of about 0.005% or about 0.01% to about 0.1% or about 0.5% or about 0.8% (w/v). Preferably, the surfactant is present in an amount less than 0.2% (w/v); and most preferably less than 0.1% (w/v).

The composition of the present invention may contain a hydrogen peroxide stabilizer. Preferably, the stabilizer is a diphosphonic acid alkanol as disclosed in U.S. Pat. No. 4,812,173. The most preferred stabilizer is diethylene triamine penta-(methylenephosphonic acid) or a physiologically compatible salt thereof. This compound is manufactured by Solutia under the name DEQUEST® 2060. The stabilizer is preferably present in the solution in an amount between about 0.001 and about 0.03% by weight of the composition, and most preferably between about 0.006 and about 0.0120% by weight of the solution. Stabilization of hydrogen peroxide in contact lens disinfection systems is described in more detail in U.S. Pat. Nos. 4,812,173 and 4,889,689, both incorporated herein by reference.

If desired, additional conventional stabilizers may be employed in conjunction with or in place of the diethylene triamine penta-(methylenephosphonic acid) if it is compatible with the material to be sterilized. Some conventional stabilizers are not compatible with the polymers typically found in contact lenses (e.g., odiumstannate), and should therefore, only be used with materials which would not be adversely affected by stannate stabilizers.

The block copolymers of the present invention may also be combined with other components commonly utilized in products for treating contact lenses, such as rheology modifiers, enzymes, antimicrobial agents, surfactants, chelating agents, buffering agents or combinations thereof.

The composition of the present invention preferably contains a buffer. The buffer maintains the pH preferably in the desired range, for example, in a physiologically acceptable range of about 4 or about 5 or about 6 to about 8 or about 9 or about 10. In particular, the solution preferably has a pH in the range of about 5 to about 8. The buffer is selected from inorganic or organic bases, preferably basic acetates, phosphates, borates, citrates, nitrates, sulfates, tartrates, lactates, carbonates, bicarbonates and mixtures thereof, more preferably basic phosphates, borates, citrates, tartrates, carbonates, bicarbonates and mixtures thereof. Typically, it is present in an amount of 0.001% to 2%, preferably 0.01% to 1%; most preferably from about 0.05% to about 0.30%.

The buffer component preferably includes one or more phosphate buffers, for example, combinations of monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate (Na2HPO4), sodium monobasic phosphate (Na2H2PO4), and potassium monobasic phosphate (KH2PO4).

The solutions of the present invention preferably include an effective amount of a tonicity component to provide the liquid medium with the desired tonicity. Such tonicity components may be present in the solution and/or may be introduced into the solution. Among the suitable tonicity adjusting components that may be employed are those conventionally used in contact lens care products, such as various inorganic salts. Sodium chloride and/or potassium chloride and the like are very useful tonicity components. The amount of tonicity component included is effective to provide the desired degree of tonicity to the solution. Such amount may, for example, be in the range of about 0.4% to about 1.5% (w/v). If a combination of sodium chloride and potassium chloride is employed, it is preferred that the weight ratio of sodium chloride to potassium chloride be in the range of about 3 to about 6 or about 8. The preferred tonicity component is sodium chloride present in the range of 0.50% to 0.90%.

Typical tonicity builders for use in the invention include suitable water soluble salts compatible with ocular tissue, preferably alkali or alkali earth metal halide, sulfates, nitrates, carbonates, borates, and phosphates, more preferably sodium or potassium chloride. The tonicity builder is present in an amount sufficient to provide a tonicity of the dosage regimen of 50 to 400 mosmol/kg, most preferably 250 to 350 mosmol/kg after neutralization of hydrogen peroxide. When non-contact lens cleaning is the desired use, the tonicity builder may also be absent or in even greater amounts than set forth above.

The contact lens can be contacted with the solution by immersing the lens in the solution. Although not necessary, the solution containing the contact lens can be agitated, for example, by shaking the container containing the solution and contact lens, to at least facilitate removal of deposit material from the lens.

The present invention, in a further aspect, provides a method of disinfecting a contact lens comprising the steps of: (a) contacting a contact lens with an aqueous solution of about 0.5 w/v % to about 6 w/v % by weight hydrogen peroxide and at least one poly(oxyethylene)-poly(oxybutylene) di-block copolymer, wherein the poly(oxyethylene)-poly(oxybutylene) block copolymer is of the formula (EO)m(BO)n, wherein EO is oxyethylene and BO is oxybutylene, and wherein m is an integer having an average value of 5 to 15 and n is an integer having an average value of 2 to 10, wherein the composition is incapable of foaming at any time within a disinfection cycle carried out in a disinfection cup having a platinum-coated plastic disk that catalytically decomposes hydrogen peroxide generating oxygen gas bubbles excessively to cause overflow of the composition from the disinfection cup, and (b) neutralizing the hydrogen peroxide by catalytic decomposition.

Methods for treating a contact lens using the herein described compositions are included within the scope of the invention. Such methods comprise contacting a contact lens with such a composition at conditions effective to provide the desired treatment to the contact lens.

The contact lens can be contacted with the solution by immersing the lens in the solution. The step of neutralizing comprises contacting the solution with a metal catalyst, for example, platinum metal catalyst.

Although not necessary, the solution containing the contact lens can be agitated, for example, by shaking the container containing the solution and contact lens, to at least facilitate removal of deposit material from the lens.

The solutions and methods of the present invention may be used in conjunction with enzymes to remove debris or deposit material from the contact lens as the solutions of the present invention have no negative effect on the proteolytic activity of enzymes, such as UNIZYME™. After such contacting step, the contact lens optionally may be manually rubbed with saline, or even rinsed without rubbing, to remove further deposit material from the lens. The cleaning method can also include rinsing the lens substantially free of the liquid aqueous medium prior to returning the lens to a wearer's eye.

The present invention may be better understood by reference to the following examples, which are provided to further illustrate certain preferred embodiments of the invention, and should in no way be construed as limiting the scope of the invention. In the following Example, various methods known to one skilled in the art may be employed to measure the contact angle for lenses according to the present invention. Exemplary methods include, but are not limited to, the Sessile method or the Captive Bubble method.

Foaming generated by EO-BO di-block copolymers was measured as a function of head-space occupied by foam (foam-height) resulting from oxygen generation during the neutralization of a buffered 3% hydrogen peroxide solution using a platinum catalyst. Formulations containing various compositions of the copolymers described here were prepared in a 3% hydrogen peroxide containing phosphate buffered system. Ten milliliters (10 mls) of each formulation was dispensed into a cylindrical cup having an approx. 20 mL volume capacity and the neutralization process initiated by capping the container with a lid also attached to two contact lens holding baskets and a stem with a platinum catalyst attached. Internal diameter and external height of the un-capped cylindrical container were 23 mm and 49 mm respectively. The foam-height (FH) was measured and recorded relative to foam movement within the capped system's head space. Any solutions having minimum-to-no foam generation were recorded as having a FH of <10%. Any solutions having the foam exceed the headspace of the container and flow out of the container were recorded to have foamed-over (F.O).

Evident from the results in the Table 1 and Table 2, excessive foaming was observed within 10 minutes of neutralization initiation with most copolymers when tested at both high and low concentrations. Excessive foaming was considered to occur if solution flowed out the container. Surprisingly, for the (EO)10(BO)5 copolymer, which shares an approximately similar EO-BO ratio as (EO)22 (BO)10, minimal-to-no foaming as well as no foam over was observed overall when tested at high and low concentrations. At much lower concentrations, the latter resulted in excessive foaming in as low polymer concentrations as a 0.008 and 0.004% within ten minutes of neutralization initiation.

TABLE 1

Results indicating foam height within the head-space of a peroxide neutralizing system containing a platinum catalyst and the EO-BO compounds (and ratios) evaluated.

| | EO/BO Ratio | 0.1% (EO)m (BO)n Foam Height (%) | | | | 0.05% (EO)m (BO)n Foam Height (%) | | | |
|---|---|---|---|---|---|---|---|---|---|
| | | 2 min | 5 min | 10 min | foamed-over | 2 min | 5 min | 10 min | foamed-over |
| $(EO)_{45}(BO)_{10}$ | 4.5 | 50 | 100 | F.O | Yes | 50 | 100 | F.O | Yes |
| $(EO)_{20}(BO)_{5}$ | 4 | 75 | 100 | F.O | Yes | 50 | 75-100 | F.O | Yes |
| $(EO)_{10}(BO)_{5}$ | 2 | <10 (minimal-to-none) | <10 (minimal-to-none) | negligible | No | <10 (minimal-to-none) | <10 (minimal-to-none) | negligible | No |
| *$(EO)_{8}(BO)_{8.5}$ | 0.9 | — | — | — | — | 10-25 | 25-50 | 75-100 | Yes |
| $(EO)_{8}(BO)_{5}$ | 1.6 | 25-50 | 100 | F.O | Yes | 10 | 10-25 | 25-50 | No |

*solubility limitations

TABLE 2

Results indicating foam height within the head-space of a peroxide neutralizing system containing a platinum catalyst and the EO-BO compounds (and ratios) evaluated

| | EO/BO Ratio | Concentration (%) | FH Description | F.O. |
|---|---|---|---|---|
| $(EO)_{22}(BO)_{10}$ | 2.2 | 0.04% | Foamed out within 10 minutes | Y |
| | | 0.024% | Foamed out within 10 minutes | Y |
| | | 0.016% | Foamed out within 10 minutes | Y |
| | | 0.008 | Foamed out within 10 minutes | Y |
| | | 0.004% | Foamed out within 10 minutes | Y |

TABLE 2-continued

Results indicating foam height within the head-space of
a peroxide neutralizing system containing a platinum catalyst
and the EO-BO compounds (and ratios) evaluated

| | EO/BO Ratio | Concentration (%) | FH Description | F.O. |
|---|---|---|---|---|
| $(EO)_{10} (BO)_5$ | 2 | 0.04% | Minimal-to-no foaming | No |
| *$(EO)_8 (BO)_{7.6}$ | 1.05 | 0.013% | <25% foaming observed | No |

TABLE 3

Molecular weights of surfactant examples evaluated for
foaming potential during peroxide neutralization.

| Compound | Mw |
|---|---|
| $(EO)_{45} (BO)_{10}$ | 2700 |
| $(EO)_{22} (BO)_{10}$ | 1688 |
| $(EO)_{20} (BO)_5$ | 1240 |
| $(EO)_{10} (BO)_5$ | 800 |
| $(EO)_8 (BO)_{8.5}$ | 964 |
| $(EO)_8 (BO)_{7.6}$ | 899 |
| $(EO)_8 (BO)_5$ | 712 |

We claim:

1. A composition for disinfecting a contact lens, comprising about 0.5 w/v % to about 6 w/v % by weight hydrogen peroxide and at least one poly(oxyethylene)-poly(oxybutylene) di-block copolymer, wherein the poly(oxyethylene)-poly(oxybutylene) di-block copolymer is of the formula $(EO)_m(BO)_n$, wherein EO is oxyethylene and BO is oxybutylene, and wherein m is 10 and n is 5, wherein the composition comprising $(EO)_m(BO)_n$ in the range of 0.001 to 0.5 weight/volume percent, wherein the composition is incapable of foaming at any time within a disinfection cycle carried out in a disinfection cup having a platinum-coated plastic disk that catalytically decomposes hydrogen peroxide generating oxygen gas bubbles excessively to cause overflow of the composition from the disinfection cup.

2. A composition according to claim 1, wherein the poly (oxyethylene)-poly (oxybutylene) di-block copolymer is of the formula:

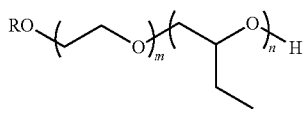

wherein R is selected from the group consisting of hydrogen, methyl, ethyl, propyl and butyl; m is 10 and n is 5.

3. A composition according to claim 1, further comprising an effective amount of a poly (oxyethylene)-poly (oxypropylene) block copolymer having the structure:

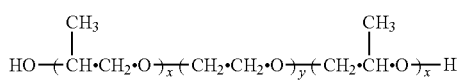

wherein x and y are integers reflecting the respective polypropylene oxide and polyethylene oxide blocks of said copolymer; and the polyoxyethylene component of the block copolymer constitutes less than 50 weight percent of the block copolymer.

4. A composition according to claim 3, wherein the polyoxyethylene component of the block copolymer constitutes about 40 weight percent of the block copolymer.

5. A composition according to claim 3, wherein the molecular weight of the polyoxypropylene block is from about 1200 and about 3100.

6. A composition according to claim 3, wherein the molecular weight of the polyoxypropylene block is about 1700.

7. A composition according to claim 3, wherein said poly (oxyethylene)-poly (oxypropylene) block copolymer is present in the range of about 0.005% to about 0.8%.

8. A composition according to claim 3, wherein said poly (oxyethylene)-poly (oxypropylene) block copolymer is present less than 0.1%.

9. A method of disinfecting a contact lens comprising the steps of:
   (a) contacting a contact lens with an aqueous solution of about 0.5 w/v % to about 6 w/v % by weight hydrogen peroxide and at least one poly(oxyethylene)-poly(oxybutylene) di-block copolymer, wherein the poly(oxyethylene)-poly(oxybutylene) di-block copolymer is of the formula $(EO)_m(BO)_n$, wherein EO is oxyethylene and BO is oxybutylene, and wherein m is 10 and n is 5, wherein the composition comprising $(EO)_m(BO)_n$ in the range of 0.001 to 0.5 weight/volume percent, wherein the composition is incapable of foaming at any time within a disinfection cycle carried out in a disinfection cup having a platinum-coated plastic disk that catalytically decomposes hydrogen peroxide generating oxygen gas bubbles excessively to cause overflow of the composition from the disinfection cup, and
   (b) neutralizing said hydrogen peroxide by catalytic decomposition.

10. A method of disinfecting a contact lens as claimed in claim 9, wherein the step of neutralizing comprises contacting said solution with a metal catalyst.

11. A method of disinfecting a contact lens as claimed in claim 10, wherein the lens is ready for insertion into the eye without a step of manually rubbing the lens.

* * * * *